United States Patent [19]

Ferguson

[11] Patent Number: 5,050,619

[45] Date of Patent: Sep. 24, 1991

[54] CONTRACEPTIVE DEVICE

[76] Inventor: Andrew R. B. Ferguson, 11 Harcourt Close, Henley-on-Thames, Oxon, RG9 1UZ, England

[21] Appl. No.: 457,698

[22] PCT Filed: Apr. 20, 1989

[86] PCT No.: PCT/GB89/00423

§ 371 Date: Dec. 22, 1989

§ 102(e) Date: Dec. 22, 1989

[87] PCT Pub. No.: WO89/10105

PCT Pub. Date: Nov. 2, 1989

[30] Foreign Application Priority Data

Apr. 20, 1988 [GB] United Kingdom ............... 8809337

[51] Int. Cl.⁵ ............................................. A61F 13/00
[52] U.S. Cl. .................................... 128/844; 128/842; 604/347
[58] Field of Search ................ 128/842, 844; 604/347, 604/349, 352

[56] References Cited

U.S. PATENT DOCUMENTS

| 2,586,674 | 2/1952 | Lonne | 128/844 |
| 4,009,717 | 3/1977 | Allen | 604/347 |
| 4,961,734 | 10/1990 | Kassman | 128/844 |

FOREIGN PATENT DOCUMENTS

| 2349361 | 4/1975 | Fed. Rep. of Germany | 604/347 |
| 2460812 | 7/1976 | Fed. Rep. of Germany | 604/347 |

Primary Examiner—Robert A. Hafer
Assistant Examiner—Charles H. Sam
Attorney, Agent, or Firm—Robert W. J. Usher

[57] ABSTRACT

A male contraceptive device has two sheaths (1, 4) which are relatively slidable for cleaning and assembly but keep stationary during use. Sheath (4) has a air hole (6) and the arrangement is such that air is allowed to and from the inner sheath via the air hole and passages between the sheaths. Air flow is partially restricted so that partial collapse of the sheaths occurs on withdrawal.

4 Claims, 2 Drawing Sheets

CONTRACEPTIVE DEVICE

This invention relates to a male contraceptive device.

The normal thin rubber sheaths, known as condoms, suffer from a number of disadvantages: (1) they sometimes break in use, (2) the Aids virus is 1000 times smaller than sperm, so, for this reason too, they do not provide a particularly secure barrier against disease, (3) they cover the penile surface with an immobile protective layer which some people find deadens most of the pleasurable stroking sensations associated with intercourse, (4) condoms do not enhance the pleasures of non-penetrative sex.

Although modifying a standard condom by increasing the thickness of the rubber would mitigate problems (1) and (2), it would exacerbate the problem of (3), and thus it would not be acceptable to many people. A condom serves no useful function (except disease prevention) during non-penetrative sex.

According to the invention there is provided a male contraceptive device comprising an inner sheath and an outer sheath within which the inner sheath fits, the sheaths being generally cylindrical in shape and substantially self-supporting, the outer sheath being closed at one end and open at the other and the inner sheath being open at the end corresponding to the open end of the outer sheath and closed at the other end except for one or more apertures, the sheaths being such that air is allowed to pass to and from the inside of the inner sheath via the aperture or apertures and the gap between the sheaths. With this arrangement friction between the two sheaths prevents movement of one sheath relative to the other: movement of the penis sliding against the inner sheath gives the sensations of intercourse, while the outer sheath provides a barrier against infection. An important feature of the design is the air channel between the two sheaths which has been developed (empirically) so as to offer suitable resistance to insertion and also withdrawal of the penis from the sheath provided that the penis is matched in size to the sheath. The thickness of the internal sheath is important, since if the inner sheath were to collapse entirely it would, by closing on itself, from an air seal, and effectively prevent withdrawal.

Satisfactory operation of this device depends on the correct design decisions as to, for example rubber thickness of both sheaths, and corrugations to maintain the right air flow between the sheaths (which must continue during all conditions of use).

Although the invention is intended primarily for use as a protective device during penetrative intercourse, it lends itself to the situation where the woman is suffering from vaginismus, thrush, or any other condition which precludes penetration, since with the invention non-penetrative use affords the male most of the sensations associated with penetrative intercourse: the reason that this is so is largely that the sheaths collapse during withdrawal, and so provide the stroking sensations associated with unprotected intercourse.

A specific embodiment of the invention will now be described by way of example with reference to the accompanying drawing in which.

Figure 1:
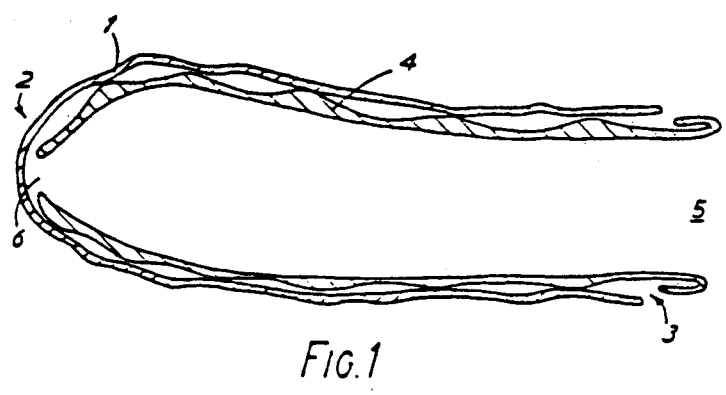
FIG. 1 shows a mid point longtitudinal cross-section through the double-sheath.
Figure 2:
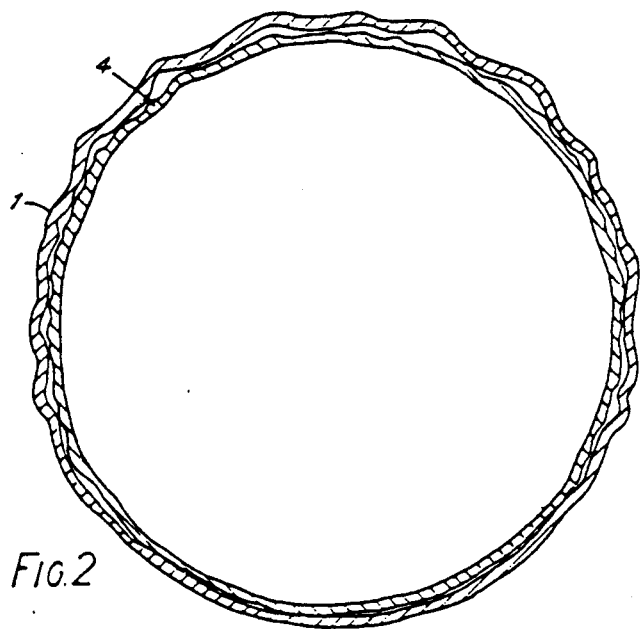
FIG. 2 shows a mid point transverse cross-section through the double-sheath to a larger scale than that of FIG. 1.

Referring to FIGS. 1 and 2 there is shown a contraceptive device comprising an outer sheath 1 of elastomeric material, preferably natural or synthetic rubber of about 1mm thickness. Sheath 1 is closed at one end 2 and open at the other end 3.

An inner sheath 4 of the same material is also of substantially cylindrical shape and fits within the outer sheath to be slidable with respect thereto for cleaning and assembly purposes, being designed to remain stationary during use. End 5 of sheath 4 is open and the other end has an air hole 6.

The inner surface of the inner sheath is relatively smooth to allow sliding within it whereas the outer surface of the inner sheath and both surfaces of the outer sheath have ripples or corrugations which may be described as veining. These enhance sensation during use. Also, they ensure that air passages are maintained between the two sheaths. This is important because it is necessary to provide that air can enter and leave the end of the inner sheath via these passages and the air hole 6. The detailed design of the corrugations which define the air passages is such that the movement of air is somewhat restricted. Thus, on withdrawal, a partial vacuum is allowed to form in the end of the inner sheath which is of such a level as to provide some degree of resistance against withdrawal and also some collapse of the sheaths. Shape restoration is allowed by re-insertion. This optimises sensation.

Figure 3:
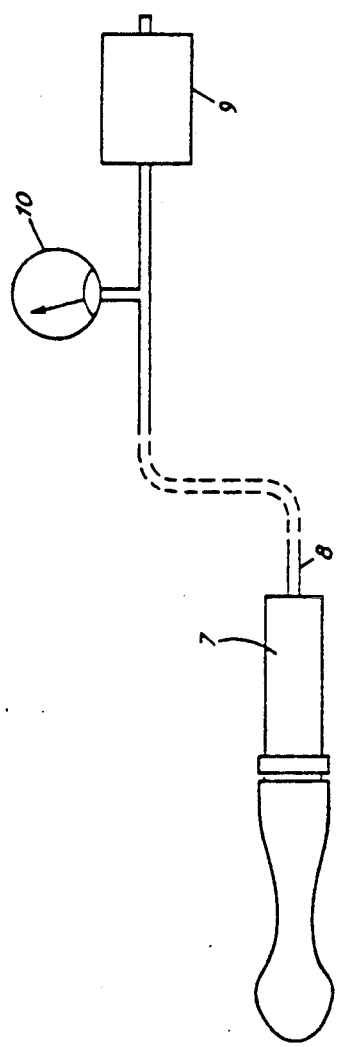
FIG. 3 shows a drawing of the device being tested with a test probe.

Referring now to FIG. 3 there is shown a test probe 7 which is of sufficient size as to provide an air seal when inserted into the device. The probe has an air passage connected to a pipe 8 whereby air can be withdrawn to establish a partial vacuum. Suction is established by a vacuum pump 9 and the partial vacuum is shown on a gauge 10. Testing establishes whether the device collapses partially under these circumstances.

I claim:

1. A male contraceptive device comprising an inner sheath and an outer sheath within which the inner sheath fits, the sheaths being generally cylindrical in shape and substantially self-supporting, the outer sheath being closed at one end and open at the other end, and the inner sheath being open at the end corresponding to the open end of the outer sheath, the sides of the inner sheath and the other end of the inner sheath being closed except for at least one aperture formed in the region of said other end, at least one of the outer surface of the inner sheath and the inner surface of the outer sheath having at least one of ripples and corrugations such that a gap is defined between the sheaths and air is allowed to pass to and from the inside of the inner sheath via said at least one aperture and said gap.

2. A contraceptive device as claimed in claim 1 wherein the sheaths are made of elastomeric material.

3. A contraceptive device as claimed in claim 2 wherein the thickness of the material is approximately 1mm.

4. A male contraceptive device comprising an outer sheath and an inner sheath, each sheath being elongate and having a generally cylindrical imperforate sidewall extending between opposite ends, the inner sheath being fitted within the outer sheath with their respective corresponding ends adjacent, the outer sheath being closed at one end and open at the other end and the inner sheath being open at the end adjacent the open end of the outer sheath and being formed with at least one aperture adjacent its other end, at least one of the outer surface of the inner sheath and the inner surface of the outer sheath having at least one of ripples and corrugations such that relative longitudinal movement of the sheaths is prevented and an air channel is defined between the sheaths, whereby a restricted movement of air to and from the inside of the inner sheath via said at least one aperture and said air channel is permitted so that a partial vacuum will be formed in the other end of the inner sheath during withdrawal from the sheath of a penis matched in size to the sheath.

* * * * *